United States Patent
Hengerer et al.

(10) Patent No.: US 9,539,136 B2
(45) Date of Patent: Jan. 10, 2017

(54) PATIENT POSITIONING TABLE HAVING A TRANSFER PLATE

(71) Applicant: Siemens Aktiengesellschaft, Munich (DE)

(72) Inventors: Arne Hengerer, Moehrendorf (DE); Markus Petsch, Erlangen (DE); Martin Requardt, Nuremberg (DE); Martin Ringholz, Erlangen (DE); Eva Rothgang, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/683,600

(22) Filed: Apr. 10, 2015

(65) Prior Publication Data

US 2015/0290066 A1    Oct. 15, 2015

(30) Foreign Application Priority Data

Apr. 11, 2014   (DE) .................. 10 2014 207 025

(51) Int. Cl.
| | |
|---|---|
| *A61G 7/07* | (2006.01) |
| *A61F 5/37* | (2006.01) |
| *A61G 13/12* | (2006.01) |
| *A61G 7/10* | (2006.01) |

(52) U.S. Cl.
CPC ............ *A61F 5/3707* (2013.01); *A61G 7/103* (2013.01); *A61G 7/1057* (2013.01); *A61G 13/121* (2013.01); *A61G 2200/32* (2013.01)

(58) Field of Classification Search
CPC .................................. A61G 7/065; A61G 7/07
USPC ....................................................... 5/621–624
See application file for complete search history.

(56) References Cited

U.S. PATENT DOCUMENTS

| | | | |
|---|---|---|---|
| 2003/0084512 A1 | 5/2003 | Fujita et al. | |
| 2005/0109346 A1* | 5/2005 | Cohen .................. | A47C 20/026 128/845 |
| 2009/0306495 A1 | 12/2009 | Scarth et al. | |

FOREIGN PATENT DOCUMENTS

| | | |
|---|---|---|
| DE | 102004047509 A1 | 4/2006 |
| WO | WO-99/11176 A1 | 3/1999 |

* cited by examiner

*Primary Examiner* — Fredrick Conley
(74) *Attorney, Agent, or Firm* — Schiff Hardin LLP

(57) ABSTRACT

A patient positioning table has a transfer plate that is reversibly transferable from the patient positioning table to a table associated with an imaging modality, and a headrest-forming extension component having a fastening section and a supporting section is provided, which can be detachably fastened to fastening devices provided on the transfer plate in exchange for a framework-like head immobilizing fixture, which can be detachably fastened to the same fastening devices.

5 Claims, 3 Drawing Sheets

PATIENT POSITIONING TABLE HAVING A TRANSFER PLATE

BACKGROUND OF THE INVENTION

Field of the Invention

The invention concerns a movable or fixed patient positioning table having a transfer plate that can be reversibly transferred from the patient positioning table to a table associated with an imaging modality.

Description of the Prior Art

As part of surgical treatment of a sedated or anesthetized patient, it is often necessary before, during and after the procedure during which the patient lies on a special treatment table, to transfer the patient to an imaging modality, in particular a magnetic resonance scanner, in order to acquire images that are used for preparing or monitoring the treatment. This transfer takes place by means of a movable or fixed patient positioning table having a transfer plate that can be reversibly transferred from the patient positioning table to the table where the surgical procedure takes place, and from which it can also be transferred to the table associated with the imaging modality. A plate changeover therefore takes place. Once the mechanical securing device has been released, the transfer plate is moved horizontally from a secure position on the respective table or patient positioning table, with the transfer positions or interfaces being designed such that the transfer plate can be moved and therefore transferred horizontally as smoothly as possible.

An example of a treatment requiring image monitoring is a neurosurgical procedure. During the procedure, the patient lies on the transfer plate that is disposed on the neurosurgical operating table. The patient's head is fixed in a head immobilizing fixture that is provided on the transfer plate. For surgery monitoring, the transfer plate is transferred from the operating table to the patient positioning table, which is then moved to the table of the magnetic resonance system where the transfer plate is transferred again. After image acquisition, the transfer plate is transferred back onto the patient positioning table and, if necessary, returned to the operating table. Another treatment example is catheter ablation, which is frequently performed under X-ray control. During the ablation process the transfer plate is disposed on the table of a C-arm X-ray machine. The guiding of the catheter can be tracked as part of the X-ray monitoring. To check the ablation success, the transfer plate is transferred again to the patient positioning table and from there to the table of the imaging modality, i.e. the MR scanner, for example, where the relevant images are then acquired.

Different transfer plates are required for the respective procedure. Whereas a neurosurgical procedure requires a transfer plate having a head immobilizing fixture in which the patient's head can be immobilized, other surgical procedures require a transfer plate having a headrest on which the patient's head is merely supported. This means in practice that, depending on a given treatment objective or depending on a given treatment modality and imaging modality between which a transfer plate changeover is to take place via the patient positioning table, a specific transfer plate has to be used or held available.

SUMMARY OF THE INVENTION

An object of the invention is to provide an improved patient positioning table compared to that described above.

This object is achieved by a patient positioning table of the general type described above, wherein a headrest-forming extension component having a fastening section and a supporting section is provided that can be detachably fastened to fastening devices provided on the transfer plate in exchange for a framework-like head immobilizing fixture that can be detachably fastened to the same fastening devices.

The patient positioning table according to the invention is distinguished by a transfer plate that, depending on requirements, can be fitted either with a framework-like head immobilizing fixture in order to perform a neurosurgical procedure, or with a headrest-forming extension component. This provides a fast and simple means of equipping the transfer plate for the particular form of surgical treatment. For a neurosurgical procedure, the framework-like head immobilizing fixture must be attached to the fastening devices; for an ablation treatment or similar, for example, for which the head merely needs to be supported, the extension component is attached to the same fastening devices. The transfer plate and hence the patient positioning table therefore can be used both for connecting a neurosurgical treatment table to the table of the imaging modality and for connecting a table assigned e.g. to a C-arm X-ray machine to the table of the imaging modality, because a simple modification of the transfer plate is possible by disposing either the extension component or the head holder depending on a given situation.

The extension component and the head holder are designed such that both can be fixed in the same fastening devices of the transfer plate. The transfer plate consequently has the basic form of a large, rectangular plate section supporting the patient's body, at one end of which plate section the corresponding fastening devices are provided. Either the head holder or the extension component, which have corresponding fastening sections for making a connection, is now fastened to the plate end.

In a further development of the invention, the extension component has a plate-like fastening section having a plurality of drilled holes and a narrower supporting section projecting therefrom, wherein the arrangement of the holes corresponds to the arrangement of the corresponding holes constituting the plate-side fastening devices. This means that a corresponding hole pattern, e.g. in the form of four holes arranged in a rectangular shape, is provided on the transfer plate or more specifically the main body of the plate. This hole pattern is replicated on the fastening section of the extension component, so that the holes automatically coincide when the fastening section is placed onto the transfer plate and corresponding connecting bolts can be passed through and secured.

Also the head immobilizing fixture, which can be fixed in the same fastening devices of the transfer plate, has a plate-like fastening section having multiple drilled holes and has a head-accommodating fixing framework projecting therefrom, wherein the arrangement of the holes corresponds to the arrangement of the plate-side holes. Here as well, the head holder can be fixed in position by simply placing the fastening sections onto the transfer plate so that the holes coincide vertically, and securing it with screws.

On the plate side, a recess corresponding to the shape of the plate-side fastening sections is advantageously provided. This recess facilitates mounting, because the respective plate-like fastening sections of the extension component or head holder can be inserted in said recess in a dimensionally compatible manner. The holes are therefore automatically congruent with respect to the plate-side holes. Moreover, the connecting structure also occupies less height, as the fastening section is countersunk in the plate recess.

The supporting section itself can be flat, but can also have a concave cross-sectional shape approximating to the rounded shape of the head so that the headrest is improved or more specifically the head is slightly stabilized laterally.

On the supporting section, padding can also be provided which can fastened to the supporting section in a fixed manner or detachably, in particular using a Velcro® fastener. This enables the head to be cushioned and therefore supported more comfortably, which is beneficial to patient comfort.

As an alternative to disposing padding on the supporting section itself, it is conceivable to provide padding extending over the entire reclining area including the supporting section. This padding is then necessarily replaceable, as it is designed to match the design of the transfer plate and associated extension component in terms of its geometry. If a head holder is disposed in place of the extension component, a different padding must be used which only extends to over the connecting region of the fastening section and main body of the plate.

DESCRIPTION OF THE PREFERRED EMBODIMENTS

Figure 1:
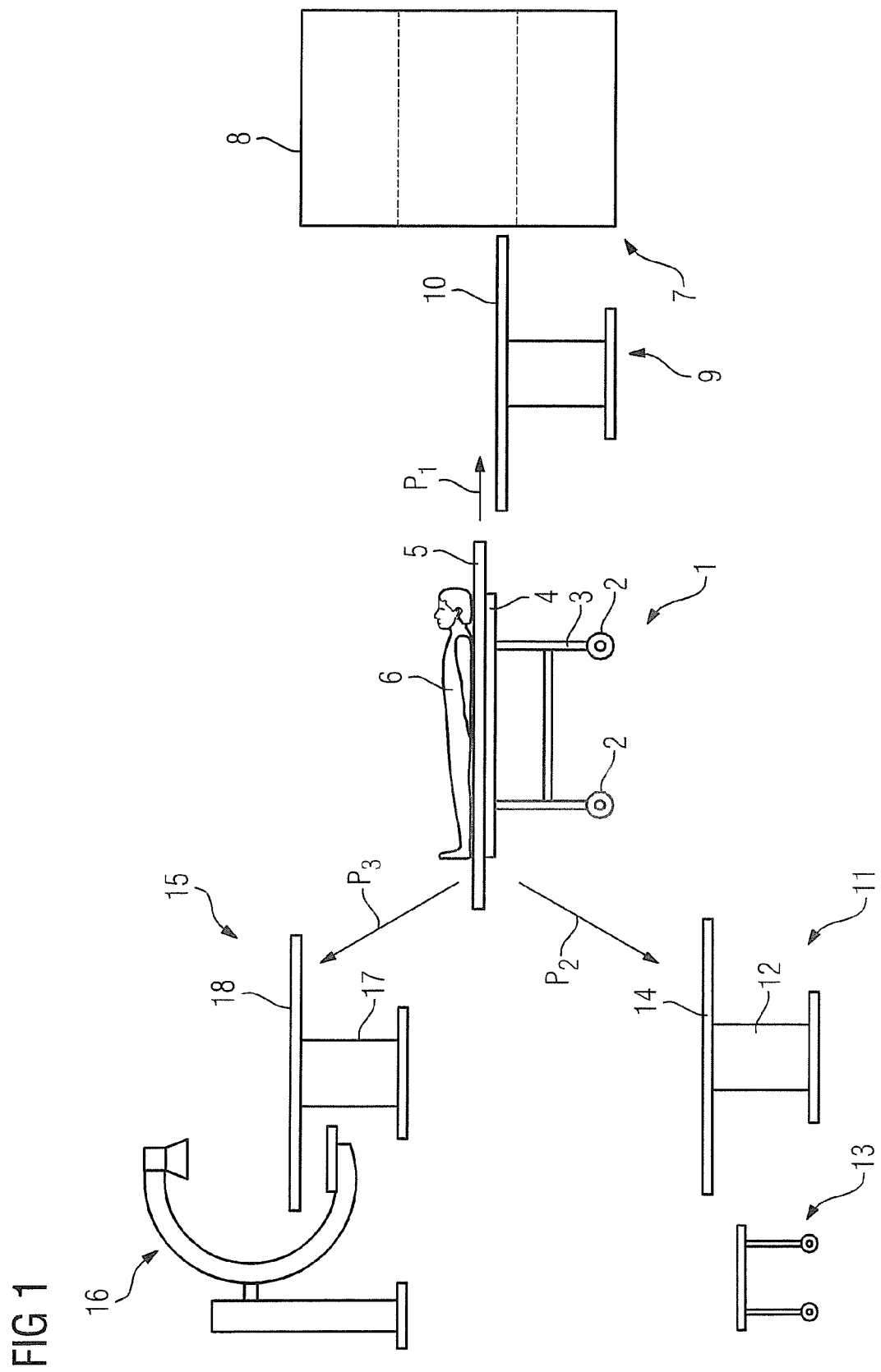
FIG. 1 schematically illustrates the complete system with a patient positioning table according to the invention and the associated treatment and imaging modalities.

FIG. 1 is a schematic illustration of a complete system having, as an example, an imaging modality and two different operating or treatment stations as well as an inventive patient positioning table having a transfer plate which can be used to transfer a patient from a treatment table to the table of the imaging modality, and vice versa.

An inventive patient positioning table 1 is shown, having a table frame 3 mounted on castors 2 and having a table top 4 and, fastened thereto in a detachable but lockable manner, a transfer plate 5 on which a patient 6 is lying in the example shown.

Also shown is an imaging modality 7, here by way of example in the form of a magnetic resonance scanner 8 having an associated table 9 with a table top 10 onto which the transfer plate can be transferred as smoothly as possible by sliding it horizontally, as indicated by the arrow P1. The patient 6 together with the transfer plate 5 can then be moved via the table 9 into the bore of the magnetic resonance scanner 8 in order to acquire images there. Self-evidently the transfer plate 5 can also be returned to the patient positioning table 1 in order to convey the patient away.

Additionally shown as an example is a first treatment or operating station 11 having a treatment table 12, the latter being, for example, an operating table for performing a neurosurgical procedure. Shown only as an example is an accessory table 13 for surgical instruments. As indicated by the arrow P2, the transfer plate 5 together with the patient 6 can be reversibly transferred from the table top 4 to the table top 14 of the table 12 by sliding the plate horizontally. For this purpose it is only necessary to move the patient positioning table 1 up to the table 12 and, after appropriate positioning and releasing of the mechanism locking the transfer plate 5 to the table top 4, to slide the transfer plate 5 horizontally so that it is accommodated onto the table top 4. A locking mechanism similar to that of the table top 10 is also possible there. The neurosurgical procedure can then be performed on the patient 6. If progress is to be monitored, the patient can be returned via the transfer plate 5 to the patient positioning table 1 and moved to the magnetic resonance scanner 8 for image monitoring purposes, etc.

In addition, a second treatment or operating station 15 is provided which is, for example, a C-arm X-ray machine 16 with associated patient table 17 which in turn has a table top 18. At a treatment modality of this kind it is possible, for example, to perform a catheter treatment while simultaneously carrying out an X-ray examination. The patient 6 can likewise be transferred in a largely jolt-free manner onto the table top 18 via the transfer plate 5, as indicated by the arrow P3. Again it is merely necessary for this purpose to roll the patient positioning table 1 to the patient table 17. After release of the locking mechanism, the transfer plate 5 can be slid onto the table top 18 where it is locked in place again. When the catheter treatment, e.g. an ablation, is complete, to verify that the treatment is successful the patient 6 can be returned to the patient positioning table 1 via the transfer plate 5 and moved therefrom to the table 9 of the magnetic resonance device 8 in order to check the success of the treatment via corresponding MR images.

With the system described it is possible, because of the inventive design of the patient positioning table 1, to use one and the same transfer plate 5 for transfer between the imaging modality 7 and the first treatment or operating station 11 and between the imaging modality 7 and the second treatment or operating station 15. The transfer plate 5, which is of course designed to be guided on corresponding sliding or linear guides of the respective table tops 10, 14 and 18, merely needs to have its attachment changed to suit the corresponding procedure-dependent positioning of the head of the patient 6.

Figure 2:
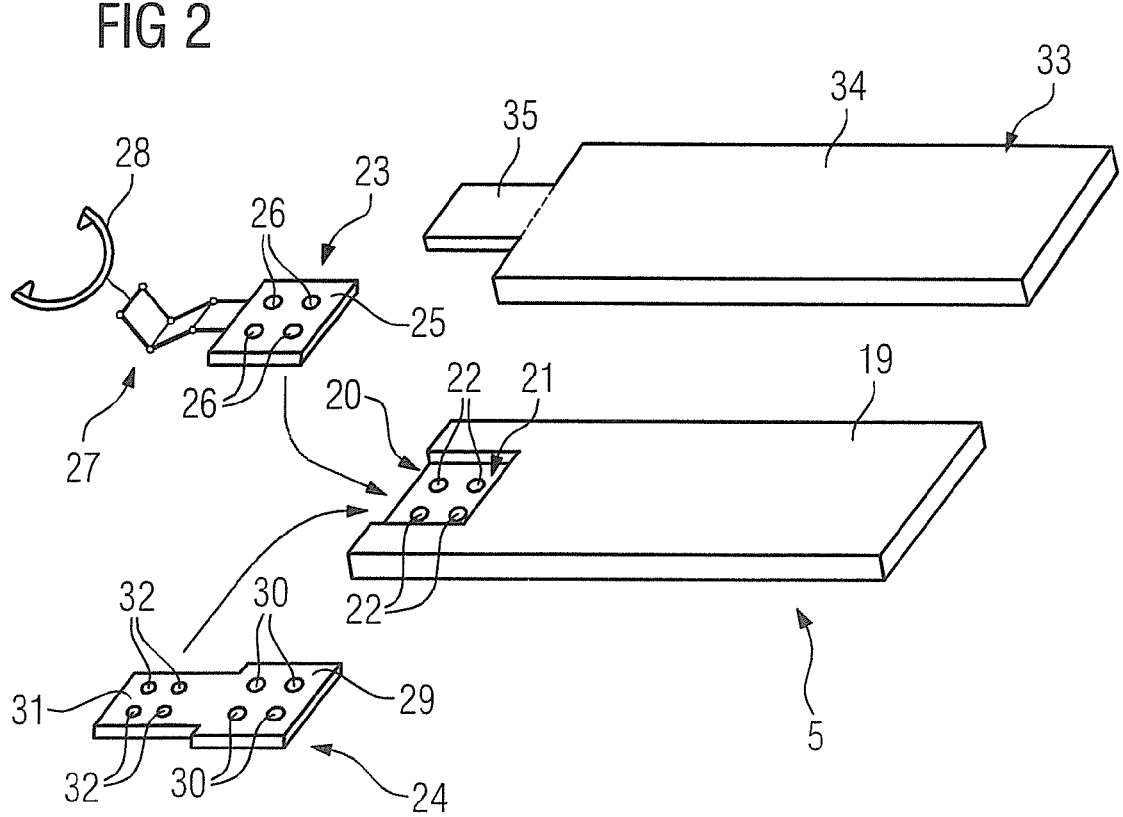
FIG. 2 is an exploded view of the transfer plate with thereon mountable extension component and head holder as well as padding.

FIG. 2 shows an inventively designed transfer plate 5 comprising a plate main body 19 on which, in the example shown, a recess 20 is provided, in the region of which fastening devices 21 in the form of four holes 22, e.g. threaded perforations, are provided. On these fastening devices 21 it is now possible, depending on the treatment in question, to dispose either a head holder 23 for a neurosurgical procedure or an extension component 24 for performing some other treatment for which the head merely needs to be supported.

The head immobilizing fixture 23 has for this purpose a plate-like fastening section 25 on which, according to the arrangement of the holes 22, likewise corresponding holes 26 arranged in the same pattern are provided. The size of the fastening section 25 corresponds to the size of the recess 20, so that is can effectively be inserted in a form-fit manner with the holes 26 being congruent with the holes 22. Using suitable fastening bolts, either in the form of through bolts which are connected to a nut on the underside of the plate or which can be screwed into the bores 22 implemented as threaded holes, the head immobilizing fixture 23 can now be disposed thereon. A retaining or fixing frame 28 in which the head of the patient 6 is clamped is movably positioned via a corresponding articulation 27. Therefore, if a neurosurgical procedure is to take place at a first treatment or operating station 11, the head immobilizing fixture 23 is attached to the plate main body 19.

However, if another treatment is to take place at the second treatment or operating station 15, e.g. an ablation or similar treatment, no special head fixation is required. Rather it is only necessary to support the head of the patient 6. To enable this, the extension component 24 is disposed on the plate main body 19. This also has a plate-like fastening section 29 whose shape corresponds to that of the recess 20 so that it can be inserted in a form-fit manner. On the fastening section 29, corresponding holes 30 are likewise provided whose hole pattern corresponds to that of the holes 22. Adjacent to the fastening section 29 is a narrower supporting section 31 on which the patient's head rests. Also shown as an example are corresponding perforations 32 to which, for example, a head coil can be fastened, as will be described in greater detail below. For the appropriate equipping of the transfer plate 5 it is therefore again merely necessary to insert the fastening section 29 in the recess 20 and then attach the corresponding fastening bolts.

Also shown is a padding 33 which is shaped according to whether the head immobilizing fixture 23 or the extension component 24 is now in place. It has a corresponding padding main body 34, which, if the head immobilizing fixture 23 is mounted, has a purely rectangular shape. This because there is then no actual supporting section, so that no padding section needs to be provided in this case. However, in the example shown such an additional padding section 35 is provided which, if the extension component 24 is mounted, overlaps the supporting section 31. The dashed line indicates by way of example that the padding 33 which must be used if the head immobilizing fixture 23 is mounted does not now have this padding section 35.

Figure 3:
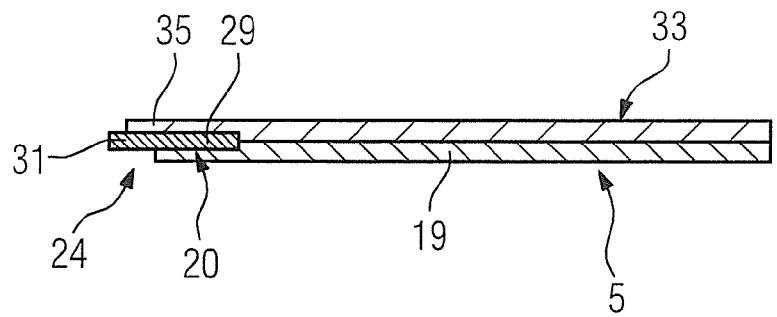
FIG. 3 is a cross section through the transfer plate having an extension component fastened thereto.

FIG. 3 shows as an example a sectional view through the transfer plate 5 on which the extension component 24 is disposed. As can be seen, the fastening section 29 lies in the recess 20 so that overall the installed height is somewhat reduced. The supporting section 31 extends away from the transfer plate 5 or more specifically the plate main body 19.

Also shown is the padding 33 which, as an example, is made somewhat thinner in the region of the padding section 35 so that the increased height due to the disposition of the extension component 24 is compensated and a flat reclining area is produced. If the head immobilizing fixture 23 were mounted, the height would be comparable, but then only the fastening section 25 would lie in the recess 20 whereas the articulation 27 together with the fixing frame 28 would extend laterally. The padding 33 would be shorter, and would be composed solely of the padding main body 34.

Figure 4:
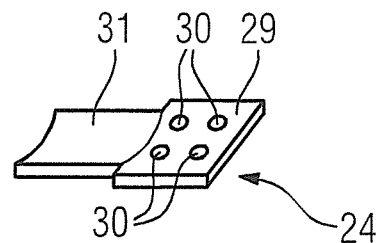
FIG. 4 is a perspective view of an extension component having a concavely recessed supporting section.

FIG. 4 shows another embodiment of an extension component 24, wherein the same reference characters are used for identical components. It again has a fastening section 29 having the holes 30 and a supporting section 31 that here has a concave, recessed shape. This enables the head to be supported in a somewhat laterally guided manner.

Figure 5:
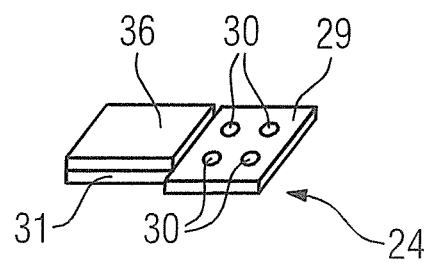
FIG. 5 is a perspective view of the extension component having thereon disposed padding of the supporting section.

FIG. 5 shows another embodiment of an extension component 24, again comprising a fastening section 29 having the holes 30, and a supporting section 31 which is here of flat design. Disposed thereon is a separate padding 36, preferably detachable, e.g. via a Velcro fastener. In other words, the padding 33 would in this case merely consist of the padding main body 34, i.e. could therefore be used both in conjunction with the extension component 24 and in conjunction with the head immobilizing fixture 23. The supporting section 31 could also be concave as shown in FIG. 4, in which case the shape of the padding 36 would conform thereto.

Figure 6:
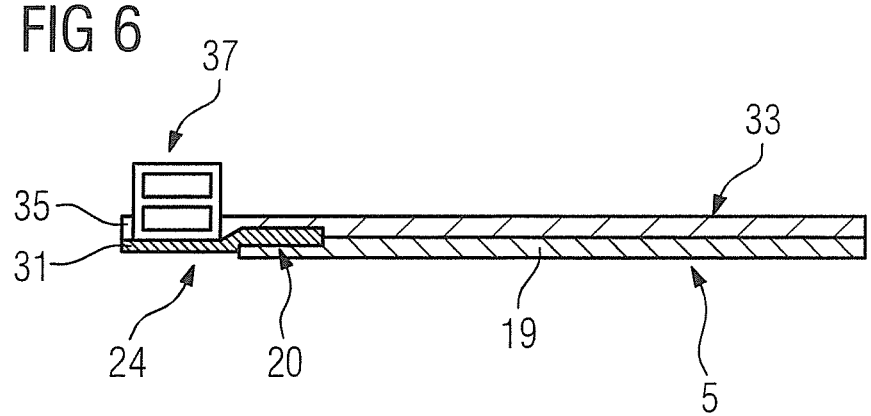
FIG. 6 is a view of a portion of a transfer plate having a head coil disposed thereon.

Lastly, FIG. 6 shows the transfer plate 5 with the thereon disposed extension component 24 and padding 33, wherein a head coil 37 disposed on or more specifically bolted to the supporting section 31 which, as shown in FIG. 2, has corresponding holes 32. The patient's head rests in the head coil 37, the padding section 35 of the padding 33 would extend through the head coil 37 so that the patient is comfortably supported. It would also be possible to provide a corresponding padding directly on the head coil 37 so that then again only one padding 33 could be used with the padding main body 34.

Although modifications and changes may be suggested by those skilled in the art, it is the intention of the inventors to embody within the patent warranted hereon all changes and modifications as reasonably and properly come within the scope of their contribution to the art.

We claim as our invention:

1. A patient positioning table comprising:
   a table body having a table surface;
   a transfer plate that is removably attachable to said surface of said table body and that is also selectively attachable to a patient support of an imaging modality, after removal from said table body;
   a headrest-forming extension component comprising an extension fastening plate connected to a head supporting section, said extension fastening plate having a plate shape and a plurality of holes therein in a hole pattern;
   a head immobilizing fixture comprising a fixture fastening plate connected to an immobilizing section, said fixture fastening plate having a plate shape and a hole pattern that are identical to said plate shape and said hole pattern of said extension fastening plate; and
   said transfer plate having a recess therein having a recess shape and a hole pattern therein that is identical to said hole position in each of said extension fastening plate, and said fixture fastening plate, making each of said headrest-forming extension component and to said head immobilizing fixture selectively attachable to and removable from said transfer plate by insertion or removal fastening elements in and from said holes in said hole pattern, allowing selective removal and exchange of said headrest-forming extension component and said head immobilizing fixture on said transfer plate.

2. A patient positioning table as claimed in claim 1 wherein said supporting section of said headrest-forming extension component has a concave cross-sectional shape.

3. A patient positioning table as claimed in claim 1 comprising padding on said supporting section of said headrest-forming extension component.

4. A patient positioning table as claimed in claim 3 wherein said padding is detachably fastened to said supporting section.

5. A patient positioning table as claimed in claim 1 comprising padding on said surface of said table body.

* * * * *